US006900246B2

(12) United States Patent
List et al.

(10) Patent No.: US 6,900,246 B2
(45) Date of Patent: May 31, 2005

(54) METHOD AND DEVICE FOR GENERATING AN AEROSOL

(75) Inventors: Klaus List, Reichelsheim (DE); Roman Messerschmid, Bonn (DE); Klaus-Jürgen Steffens, Rheinbach (DE); Manfred Wolf, Schöneberg (DE)

(73) Assignee: Buender Glas GmbH, Buende (DE)

( * ) Notice: Subject to any disclaimer, the term of this patent is extended or adjusted under 35 U.S.C. 154(b) by 0 days.

(21) Appl. No.: 10/045,835

(22) Filed: Jan. 11, 2002

(65) Prior Publication Data

US 2002/0107293 A1 Aug. 8, 2002

(30) Foreign Application Priority Data

Jan. 11, 2001 (DE) ........................................ 101 00 867

(51) Int. Cl.[7] .............................. B01F 3/04; B01F 3/06; B05B 7/00; A61M 11/00

(52) U.S. Cl. .............................. 516/7; 516/6; 261/78.2; 261/DIG. 78; 128/200.14; 128/200.16; 239/8; 239/338

(58) Field of Search ........................ 516/6, 7; 261/78.2, 261/DIG. 78; 239/8, 338; 128/200.14, 200.16, 400.14, 400.16

(56) References Cited

U.S. PATENT DOCUMENTS 2,873,756 A * 2/1959 Pool ........................ 137/87.04
4,206,158 A * 6/1980 Wood .................. 261/DIG. 78
4,267,974 A * 5/1981 Kienholz et al. ........... 239/338
4,268,460 A * 5/1981 Boiarski et al. ............ 239/338
4,278,446 A * 7/1981 Von Rosenberg et al. 48/197 R
4,294,208 A * 10/1981 Wagner ...................... 123/285
4,506,834 A * 3/1985 Ek ................................ 241/1
4,552,893 A * 11/1985 Gleason et al. ............. 514/560
4,578,102 A * 3/1986 Colmon et al. ............... 65/114
4,625,916 A * 12/1986 Nieuwkamp et al. ....... 239/431
4,690,332 A * 9/1987 Hughes ...................... 239/338
4,972,830 A * 11/1990 Wong et al. ........... 128/200.21
5,096,917 A * 3/1992 Sallmann et al. ........... 514/415
5,349,947 A * 9/1994 Newhouse et al. .... 128/203.21
6,338,443 B1 * 1/2002 Piper .......................... 239/338

OTHER PUBLICATIONS

Sanders, "Principles of Aerosol Technology", (Van Nostrand Reinhold Company, NY, NY, copyright 1970) pp. 11 and 18–33, May 1974.*

* cited by examiner

*Primary Examiner*—Daniel S. Metzmaier
(74) *Attorney, Agent, or Firm*—Laurence A. Greenberg; Werner H. Stemer; Ralph E. Locher

(57) ABSTRACT

A method for generating an aerosol includes the step of guiding a gas which flows at supersonic velocity and which has input particles suspended therein in such a way that a compression shock occurs. The input particles are broken down into smaller output particles upon crossing the compression shock. A device for generating an aerosol is also provided.

29 Claims, 1 Drawing Sheet

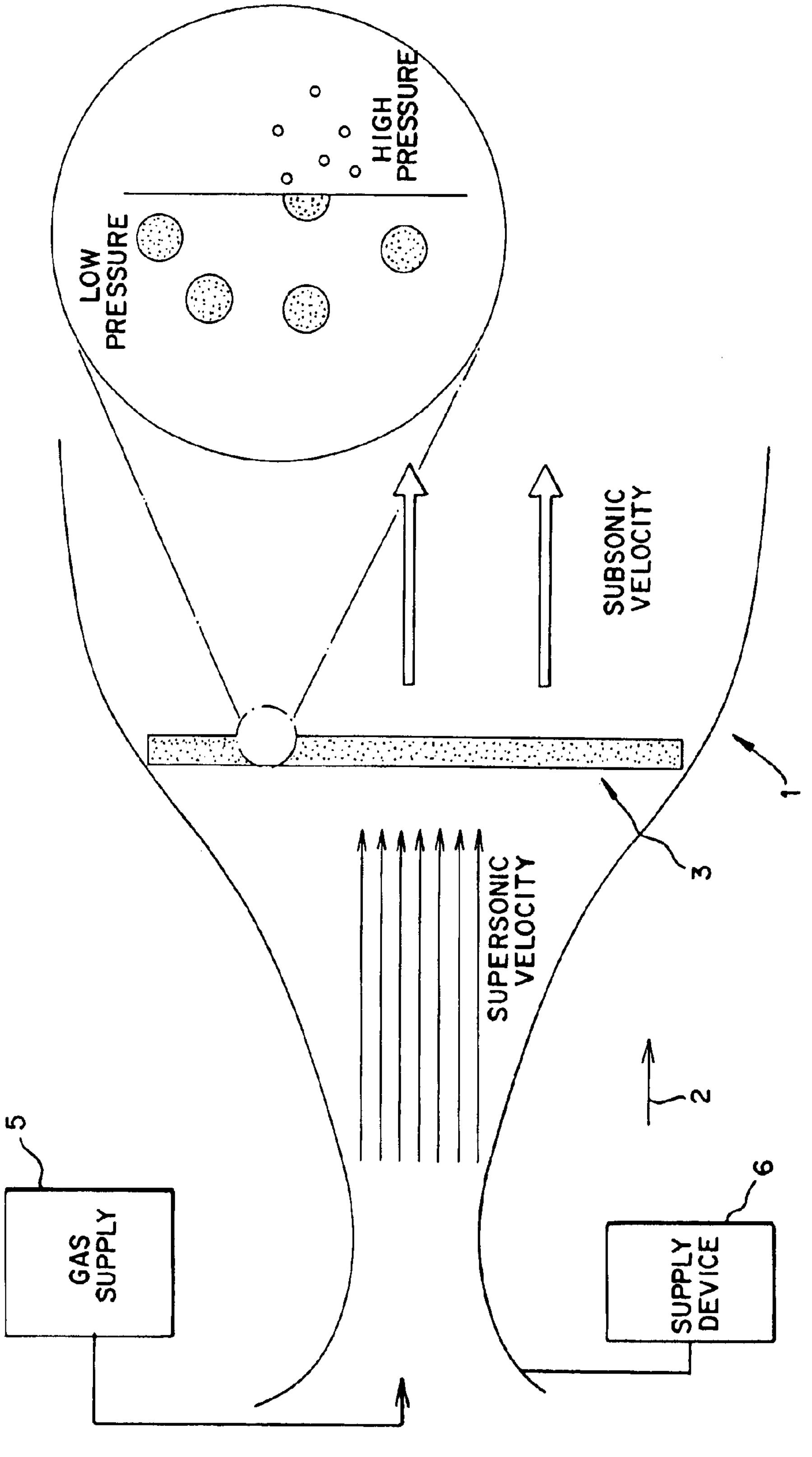
LOW PRESSURE
HIGH PRESSURE
SUBSONIC VELOCITY
SUPERSONIC VELOCITY
1
3
2
5
GAS SUPPLY
6
SUPPLY DEVICE

METHOD AND DEVICE FOR GENERATING AN AEROSOL

BACKGROUND OF THE INVENTION

FIELD OF THE INVENTION

The present invention relates to a method and device for generating an aerosol.

For a variety of technical and medical applications it is necessary to have liquid or solid particles uniformly distributed in a finely divided state through a gas. Such aerosol particles may have various diameters and for specific applications it is desired to have aerosol particles of a given diameter.

SUMMARY OF THE INVENTION

It is an object of the invention to provide a method and a device for generating an aerosol which allows to break up previously generated liquid particles and/or loosely linked solid particles (input particles) into substantially smaller output particles in the form of an aerosol.

With the foregoing and other objects in view there is provided, in accordance with the invention, a method for generating an aerosol, which includes the steps of:

guiding a gas having input particles suspended therein and flowing at a supersonic velocity such that a compression shock occurs in the gas; and breaking the input particles into output particles being smaller than the input particles by passing the input particles through the compression shock.

According to another mode of the invention, the gas is guided in an enclosure having a cross-section widening in a direction of flow in order to achieve the supersonic velocity.

According to yet another mode of the invention, the enclosure is provided such that, as seen in the direction of flow, the cross-section of the enclosure narrows prior to widening in order to achieve a sonic velocity.

According to another mode of the invention, the gas is guided such that the compression shock occurs, as seen in the direction of flow, before an end of the enclosure and thus inside the enclosure.

According to a further mode of the invention, the gas is guided such that the compression shock occurs at a point located substantially ⅔ of a distance along a length of a widening portion of the enclosure following a narrowest cross-section of the enclosure in the flow direction.

According to another mode of the invention, the gas is guided such that the compression shock occurs, as seen in the direction of flow, behind an end of the enclosure and thus outside the enclosure.

According to another mode of the invention, the input particles are fed to the gas while the gas is at rest or at subsonic velocity.

With the objects of the invention in view there is also provided, a device for generating an aerosol, including:

a gas guiding device configured to guide a gas having input particles suspended therein and flowing at a supersonic velocity; and the gas guiding device being configured to generate a compression shock in the gas such that the input particles, upon crossing the compression shock, are broken down into output particles smaller than the input particles.

According to another feature of the invention, the gas guiding device includes an enclosure defining a flow direction, the enclosure guides the gas along the flow direction, the enclosure has a first portion with a narrowest cross-section and a second portion disposed after the first portion as seen in the flow direction, the second portion has a cross-section expanding along the flow direction.

According to yet another feature of the invention, the enclosure includes a third portion disposed upstream of the first portion as seen in the flow direction, the third portion has a cross-section narrowing along the flow direction.

According to another feature of the invention, the gas guiding device is a Laval nozzle.

According to yet another feature of the invention, the gas guiding device is an unmatched Laval nozzle.

According to another feature of the invention, a supply device is connected to the gas guiding device, the supply device supplying the input particles. The supply device may for example be an atomizer.

According to another feature of the invention, a supply device for supplying the input particles is disposed upstream of the narrowest cross-section of the first portion of the enclosure.

According to yet another feature of the invention, a supply device for supplying the input particles is disposed upstream of the cross-section of the third portion narrowing along the flow direction.

According to another feature of the invention, a gas supply device is connected to the gas guiding device for providing pressurized gas. The gas supply device may be a storage tank or a pump.

According to a further feature of the invention, the gas has a pressure between $1 \cdot 10^5$ Pa and $2.5 \cdot 10^7$ Pa, preferably between $2 \cdot 10^5$ Pa and $2 \cdot 10^6$ Pa, even more preferably between $3 \cdot 10^5$ Pa and $1 \cdot 10^5$ Pa, or substantially a pressure of $5 \cdot 10^5$ Pa in a resting state upstream of the cross-section of the third portion of the gas guiding device narrowing along the flow direction.

According to a further feature of the invention, the gas has a temperature between −20° C. and 400° C., preferably between 0° C. and 50° C., even more preferably between 10° C. and 30° C. or between 20° C. and 25° C. in a resting state upstream of the cross-section of the third portion of the gas guiding device narrowing along the flow direction.

According to yet a further feature of the invention, the gas is air, $N_2$, $O_2$, or $CO_2$ or a combination of these gases.

According to another feature of the invention, the input particles have an average size between 20 μm and 200 μm, preferably between 40 μm and 100 μm, and even more preferably between 45 μm and 60 μm.

According to another feature of the invention, the output particles have an average size between 1 μm and 10 μm, preferably between 2 μm and 5 μm, and also preferably of substantially 3 μm.

According to another feature of the invention, droplets of a liquid are supplied as the input particles.

According to yet another feature of the invention, water is provided as the liquid.

According to another feature of the invention, the liquid is used as a carrier liquid for an agent, such as a pharmacologically active agent, in particular a pharmacologically active inhalation therapy agent.

According to another feature of the invention, a solvent such as alcohol is provided as the liquid.

According to yet another feature of the invention, a combustible liquid such as a fuel is provided as the liquid.

According to another feature of the invention, at least some of the input particles are loosely linked particles including solid particles and/or semi-solid particles.

Other features which are considered as characteristic for the invention are set forth in the appended claims.

Although the invention is illustrated and described herein as embodied in a method and a device for generating an aerosol, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawing.

BRIEF DESCRIPTION OF THE DRAWING

The single FIGURE is a diagrammatic side view of a gas flow region for illustrating the method and the device according to the invention.

DESCRIPTION OF THE PREFERRED EMBODIMENTS

Referring now to the single FIGURE in detail, there is shown a schematic side view (i.e. sectional view) of an inner contour of a part of a nozzle 1 in which a gas flows in a flow direction indicated by arrow 2. The nozzle 1 expands in the flow direction. In other words, the cross-section of the nozzle—that is to say, its inner cross-sectional area—increases in the flow direction.

Located in front of, i.e. upstream of the widening part of the (planar or round) nozzle 1 is a converging portion and a narrowest portion or throat at the transition to the diverging portion. In the operation of this type of nozzle (also known as a Laval nozzle), a flow with sonic velocity builds in the narrowest portion of the nozzle beginning at a defined pressure ratio (ratio of the pressure in front of the converging portion to the pressure in the environment behind the diverging portion), while supersonic flow prevails in the diverging portion of the nozzle. In the present example, the gas which is fed to the nozzle at its converging portion is supplied having a static pressure of approx. $5 \cdot 10^5$ Pa, the gas being supplied by a gas supply 5. The gas may for example be drawn from a pressure vessel or may be provided by a compressor. The temperature of the pressure gas prior to being discharged into the nozzle is approximately room temperature, i.e. 20° C. to 30° C.

A supply device 6 for feeding in input particles, with the aid of which the particles that are to be broken up or split into pieces are fed in and suspended in the gas, is disposed at a suitable location, namely in front of the narrowest portion of the nozzle. The supply device 6 can be formed of a pump atomizer with which a relatively coarse drop spectrum is suspended in the gas stream. An alternative or additional technique is to feed into the gas flowing at supersonic velocity. Depending on the field of application of the generated aerosol, the input particles can be droplets of liquid such as water with or without added agents, or a solvent such as alcohol. Alternatively, it can be provided that the input particles are fuel droplets, for instance for a combustion engine or a firing plant. Finally, possibly in addition to droplets, the input particles can be loosely linked solid or semi-solid particles which will be broken down into (substantially) smaller particles.

The nozzle 1 is constructed in known fashion taking into account the pressure relation in which it will be operated, so that in the course of its diverging portion an underpressure relative to the environment results, i.e. relative to the space adjacent the end of the nozzle 1 ("unmatched nozzle"), as a result of which a compression shock 3 arises in the nozzle as represented in the figure.

Surprisingly, it has been found that the input particles carried by the gas flowing through the nozzle are broken down into a spectrum of substantially smaller particles or droplets upon passing through the compression shock, which contains a very large pressure gradient (pressure rise in a narrow space). For instance, when the core region of the compression shock, i.e. the region with the largest pressure gradient, has had a thickness of 40 μm to 50 μm in the flow direction, a resulting mean droplet diameter (logarithmic normal distribution) of between 3 μm and 10 μm has been observed, whereas the input particles have been droplets with a significantly larger diameter, such as 50 μm.

Given an input pressure of approximately $5 \cdot 10^5$ Pa and an input temperature of approximately 300 K, a Laval nozzle whose narrowest cross-section is approximately 0.03 $cm^2$ yields a pressure of approx. $2.5 \cdot 10^5$ Pa and a temperature of approximately 250 K at the narrowest portion or throat of the nozzle. Given widening of the cross-section to approximately 0.16 $cm^2$, the flow velocity increases to 3.4 times the speed of sound (Mach 3.4), while the pressure drops to approx. $1 \cdot 10^4$ Pa and the temperature drops to less than 100 K. A compression shock effectuates a sudden pressure rise approximately to the ambient pressure ($1 \cdot 10^5$ Pa), while the temperature rises approximately the same way to the ambient temperature.

It is assumed that the extremely large pressure gradient within the compression shock leads to a crushing or ripping apart of the incoming input particles, whose diameter is on the order of magnitude of the thickness of the compression shock.

Whereas the figure represents a situation in which the compression shock is located in front of the end of the nozzle facing in the flow direction, i.e. inside the nozzle, situations in which one or more compression shocks lie outside the nozzle are also possible.

The wall friction of the gas in the region of the inner wall surface of the nozzle gives rise to slanted (i.e. angled) compression shocks, which facilitates the desired crushing effect in that the particles dwell in the compression shocks for longer periods.

We claim:

1. A method for generating an aerosol, the method which comprises:
   providing a gas supplied with input particles;
   providing an enclosure having a cross-section continuously widening in a direction of flow and towards, an end of the enclosure to achieve a supersonic velocity;
   guiding the gas with the input particles and causing the gas to flow at the supersonic velocity to cause a compression shock to occur downstream of the end and outside of the enclosure; and
   breaking the input particles into output particles being smaller than the input particles by passing the input particles through the compression shock, generating the aerosol.

2. The method according to claim 1, which comprises providing the enclosure, as seen in the direction of flow, with the cross-section of the enclosure narrowing prior to widening in order to achieve a sonic velocity.

3. The method according to claim 1, which comprises feeding the input particles to the gas while the gas is at rest.

4. The method according to claim 1, which comprises feeding the input particles to the gas while the gas flows at subsonic velocity.

5. The method according to claim 1, which comprises:

providing the enclosure with a narrowing cross-section upstream of a widening cross-section as seen in a direction of flow; and providing the gas such that a pressure of the gas in a resting state upstream of the narrowing cross-section is between $1\cdot10^5$ Pa and $2.5\cdot10^7$ Pa.

6. The method according to claim 1, which comprises:

providing the enclosure with a narrowing cross-section upstream of a widening cross-section as seen in a direction of flow; and providing the gas such that a pressure of the gas in a resting state upstream of the narrowing cross-section is between between $2\cdot10^5$ Pa and $2\cdot10^6$ Pa.

7. The method according to claim 1, which comprises:

providing the enclosure with a narrowing cross-section upstream of a widening cross-section as seen in a direction of flow; and providing the gas such that a pressure of the gas in a resting state upstream of the narrowing cross-section is between $3\cdot10^5$ Pa and $1\cdot10^6$ Pa.

8. The method according to claim 1, which comprises:

providing the enclosure with a narrowing cross-section upstream of a widening cross-section as seen in a direction of flow; and providing the gas such that a pressure of the gas in a resting state upstream of the narrowing cross-section is substantially $5\cdot10^5$ Pa.

9. The method according to claim 1, which comprises:

providing the enclosure with a narrowing cross-section upstream of a widening cross-section as seen in a direction of flow; and providing the gas such that a temperature of the gas in a resting state upstream of the narrowing cross-section is between −20° C. and 400° C.

10. The method according to claim 1, which comprises:

providing the enclosure with a narrowing cross-section upstream of a widening cross-section as seen in a direction of flow; and providing the gas such that a temperature of the gas in a resting state upstream of the narrowing cross-section is between 0° C. and 50° C.

11. The method according to claim 1, which comprises:

providing the enclosure with a narrowing cross-section upstream of a widening cross-section as seen in a direction of flow; and providing the gas such that a temperature of the gas in a resting state upstream of the narrowing cross-section is between 10° C. and 30° C.

12. The method according to claim 1, which comprises:

providing the enclosure with a narrowing cross-section upstream of a widening cross-section as seen in a direction of flow; and providing the gas such that a temperature of the gas in a resting state upstream of the narrowing cross-section is between 20°0 C. and 25° C.

13. The method according to claim 1, which comprises providing the gas such that the gas includes at least one element selected from the group consisting of air, $N_2$, $O_2$, and $CO_2$.

14. The method according to claim 1, which comprises providing the input particles such that an average size of the input particles is between 20 μm and 200 μm.

15. The method according to claim 1, which comprises providing the input particles such that an average size of the input particles is between 40 μm and 100 μm.

16. The method according to claim 1, which comprises providing the input particles such that an average size of the input particles is between 45 μm and 60 μm.

17. The method according to claim 1, which comprises providing the output particles such that an average size of the output particles is between 1 μm and 10 μm.

18. The method according to claim 1, which comprises providing the output particles such that an average size of the output particles is between 2 μm and 5 μm.

19. The method according to claim 1, which comprises providing the output particles such that an average size of the output particles is substantially 3 μm.

20. The method according to claim 1, which comprises providing the input particles as droplets of a liquid.

21. The method according to claim 20, which comprises providing water as the liquid.

22. The method according to claim 20, which comprises providing the liquid as a carrier liquid for an agent.

23. The method according to claim 22, which comprises providing the agent as a pharmacologically active agent.

24. The method according to claim 22, which comprises providing the agent as a pharmacologically active inhalation therapy agent.

25. The method according to claim 22, which comprises providing a solvent as the liquid.

26. The method according to claim 25, which comprises providing an alcohol as the solvent.

27. The method according to claim 20, which comprises providing a combustible liquid as the liquid.

28. The method according to claim 27, which comprises providing a fuel as the combustible liquid.

29. The method according to claim 1, which comprises providing at least some of the input particles as loosely linked particles selected from the group consisting of solid particles and semi-solid particles.

* * * * *